United States Patent [19]

Curtze et al.

[11] Patent Number: 5,677,303
[45] Date of Patent: Oct. 14, 1997

[54] ENOLETHERS AND THEIR USE AS A FUNGICIDE

[75] Inventors: Juergen Curtze, Geisenheim; Guido Albert, Hackenheim, both of Germany

[73] Assignee: American Cyanamid Company, Madison, N.J.

[21] Appl. No.: 670,252

[22] Filed: Jun. 20, 1996

[51] Int. Cl.$^6$ .......................... A01N 37/36; A01N 43/84; C07C 235/34; C07D 295/192
[52] U.S. Cl. ...................... 514/237.5; 514/618; 514/622; 544/158; 544/174; 564/162; 564/171
[58] Field of Search ..................................... 544/158, 174; 564/162, 171; 514/237.5

[56] References Cited

U.S. PATENT DOCUMENTS

| | | |
|---|---|---|
| 4,753,934 | 6/1988 | Nickl et al. |
| 4,910,200 | 3/1990 | Curtze et al. |
| 4,954,497 | 9/1990 | Kamikado et al. |
| 5,374,604 | 12/1994 | Kleeman et al. |

FOREIGN PATENT DOCUMENTS

| | | |
|---|---|---|
| 88-22272 | 3/1989 | Australia . |
| 307762 | 3/1989 | WIPO . |
| WO 94/22833 | 10/1994 | WIPO . |

*Primary Examiner*—Robert W. Ramsuer
*Attorney, Agent, or Firm*—Charles F. Costello, Jr.

[57] ABSTRACT

Enolethers and thioenolethers of formula I

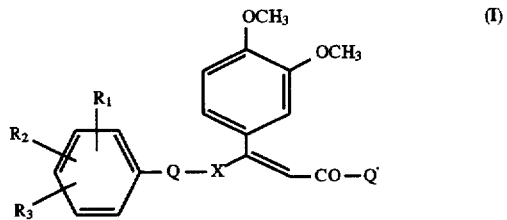

are disclosed. The compounds are useful for combatting phytopathogenic fungi.

15 Claims, No Drawings

ENOLETHERS AND THEIR USE AS A FUNGICIDE

BACKGROUND AND SUMMARY OF THE INVENTION

This invention relates to enol- and thioenolethers, and their use as a fungicide. The prior art discloses acrylic acid amides, e.g. compounds of the following formula

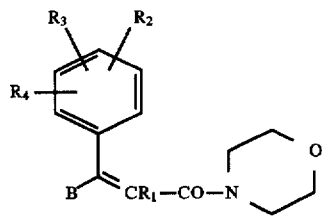

wherein $R_1$ may represent a hydrogen atom, $R_2/R_3/R_4$ may represent 3,4-dimethoxy and B may represent a benzyl group. The compounds can be used as fungicides.

It has now been found that compounds of formula I

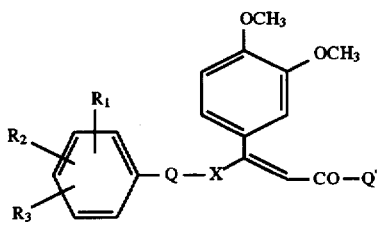

wherein Q represents a group of formula $(CH_2)_m$ (wherein m is 2 or 3) or CH—R (wherein R represents a hydrogen atom, a phenyl or a straight or branched $C_1$-$C_4$ alkyl group); Q' represents a morpholin-4-yl, a dimethylamino, methyl-ethylamino or diethylamino group; $R_1$ represents a hydrogen or halogen atom, a phenyl or a straight or branched $C_1$-$C_6$ alkyl or alkoxy group optionally substituted by one or more halogen atoms; $R_2$ and $R_3$ independently represent a hydrogen or halogen atom, a straight or branched $C_1$-$C_6$ alkyl or alkoxy group optionally substituted by one or more halogen atoms; and X represents an oxygen or sulphur atom, exhibit a high degree of fungicidal activity, when contrasted with the known, prior art compounds.

Within the above definitions Q is preferrably the group CH—R, wherein R particularly represents a hydrogen atom, and Q' morpholinyl. $R_1$ is preferrably a substituent in the para-position of the phenyl ring and X an oxygen atom. If $R_1$ represents an alkyl or alkoxy group substituted by halogen, the halogen is preferrably fluorine. Particularly preferred are compounds, wherein $R_1$ represents a chlorine atom, a trifluoromethyl or trifluoromethoxy group, a phenyl or a $C_1$-$C_4$-, more particularly $C_3$-$C_4$-alkyl or -alkoxy group. At least one of $R_2$ and $R_3$ or both preferrably represent a hydrogen atom.

The compounds of formula I can exist in form of cis and trans isomers (E- and Z-form). The synthesis of the new compounds leads to E/Z-mixtures. Under the influence of light, an equilibrium of the E-isomer and the Z-isomer is formed. The E/Z-ratio can be determined by NMR-spectroscopy. All definitions and claims herein are directed to the pure isomers as well as to their mixtures, unless otherwise stated.

To prepare a compound of formula I, the preferred starting material is the compound of formula II:

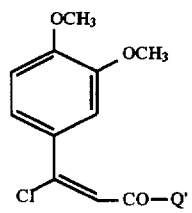

wherein Q' is defined as above, which is reacted with a alcohol or thiol of formula III:

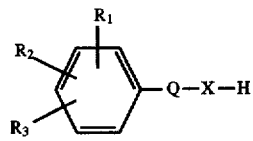

wherein $R_1$, $R_2$, $R_3$, Q and X are as defined above, in the form of their alkali metal salt, e.g., their sodium salt. The reaction is carried out preferrably in a solvent inert to the compounds to be reacted under the reaction conditions (e.g. lower alcohols or other polar solvents such as dimethylformamide or mixtures of such solvents) at temperatures between room temperature and the boiling temperature of the reaction mixture. The product of the reaction can be isolated by usual methods, e.g. by chromatography, which can also be used for the isolation of the E- and Z-isomers.

The compounds of formulae II and II are known or can otherwise be prepared by methods known in the prior art. Thus the compound of formula II may be prepared by reacting 3,4-dimethoxybenzaldehyde with a solution prepared from sodium hydride and phosphonoacetic acid triethyl ester in tetrahydrofuran. The resulting acrylic acid derivative is reacted with bromine to give 2,3-dibromo-3-(3,4-dimethoxyphenyl)propionic acid ethyl ester which is treated with potassium hydroxide in ethanol to form the corresponding propynoic acid of formula

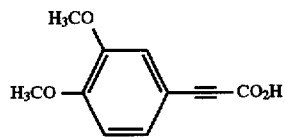

This acid is treated with excess thionylchloride. The remaining thionylchloride is removed and the resulting product is reacted with a compound of formula H—Q', e.g. morpholine, to give the compound of formula II.

Specific embodiments of the invention are as follows:
1. A compound of the formula

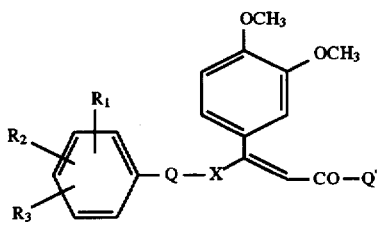

wherein Q represents a group of formula $(CH_2)_m$ (wherein m is 2 or 3) or CH—R (wherein R represents a hydrogen atom, a phenyl or a straight or branched $C_1$-$C_4$ alkyl group); Q' represents a morpholin-4-yl, a dimethylamino, methyl-ethylamino or diethylamino group; $R_1$ represents a hydrogen or halogen atom, a

3 phenyl or a straight or branched $C_1-C_6$ alkyl or alkoxy group optionally substituted by one or more halogen atoms; $R_2$ and $R_3$ independently represent a hydrogen or halogen atom, a straight or branched $C_1-C_6$ alkyl or alkoxy group optionally substituted by one or more halogen atoms; and X represents an oxygen or sulphur atom.

2. A compound according to embodiment 1, wherein Q' represents morpholin-4-yl.
3. A compound according to embodiment 1, wherein Q represents CH—R and R is a hydrogen atom.
4. A compound according to embodiment 1, wherein X represents an oxygen atom.
5. A compound according to embodiment 1, wherein $R_3$ is a hydrogen atom.
6. A compound according to embodiment 1, wherein $R_2$ and $R_3$ both are hydrogen atoms.
7. A compound according to embodiment 1, wherein $R_1$ represents a hydrogen, fluorine, chlorine or bromine atom, $C_1-C_4$ alkyl or alkoxy group, a phenyl group, or a trifluoromethyl or trifluoromethoxy group.
8. A compound according to embodiment 1, wherein $R_2$ and $R_3$ are hydrogen atoms and $R_1$ represents a hydrogen or fluorine, chlorine or bromine atom, a $C_1-C_4$ alkyl or alkoxy group, a trifluoromethyl or trifluoromethoxy group.
9. 3-(4-Chlorobenzyloxy)-3-(3,4-dimethoxyphenyl)-1-morpholin-4-ylprop-2-en-1-one as either an E or Z isomer, or as a mixture comprising the E and Z isomer.
10. 3-(4-i-Propylbenzyloxy)-3-(3,4-dimethoxyphenyl)-1-morpholin-4-ylprop-2-en-1-one, as either an E or Z isomer, or as a mixture comprising the E and Z isomer.
11. A process for preparing the compound according to embodiment 1 which comprises reacting a compound of formula

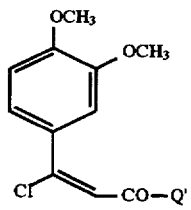

(II)

with an alcohol or thiol of formula

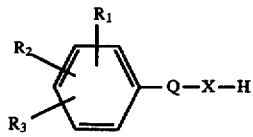

(III)

in the form of an alkali metal salt, to form either an E or Z isomer, or a mixture comprising the E or Z isomer; and
isolating the E or Z isomer, or mixture by crystallisation or chromatography.
12. A fungicidal composition comprising a compound of embodiment 1, and either or both, a carrier and additive.
13. A method of combating fungi at a locus which comprises treating the locus with an effective amount of the compound of embodiment 1.
14. A method of using an effective amount of the compound of embodiment 1 comprising applying a composition of said compound to phytopathogenic fungi in agriculture.
15. The method of embodiment 15 wherein the phytopathogenic fungi is *Phytophthora infestans* or *Plasmopara viticola*.

DETAILED DESCRIPTION OF THE INVENTION

The compounds of the invention are excellent fungicides, especially for the control of phytopathogenic fungi e.g. Oomycetes in agriculture. They are particularly useful for the control of *Phytophthora infestans* and *Plasmopara viticola* (grape downy mildew). Due to excellent plant tolerance, the compounds may be used in all cultivation of plants where infection by the controllable fungi is not desired. The absence of target crop phytotoxicity at fungus control rates is a feature of the present invention.

The present invention also provides a fungicidal composition which comprises a compound of formula I as defined hereinabove and an agriculturally acceptable carrier. Said composition may contain one or more compounds of the present invention. Preferably, at least one carrier in a composition according to the invention is a surface-active agent. For example, the composition may contain at least two carriers, at least one of which is a surface-active agent.

The compounds according to formula I may be applied as technical material, however, said compounds are preferably applied as a composition comprising, besides the formula I compounds, adjuvants and auxiliaries which are known for formulation purposes and are manufactured into e.g. emulsion concentrates, solutions which may be sprayed directly or diluted, diluted emulsions, wettable powders, soluble powders, dusts, granulates, microencapsulates by well-established procedures. The form of application such as spraying, atomizing, dispersing, pouring may be chosen like the compositions according to the desired objectives and the given circumstances.

It is contemplated, compounds of formula I may be formulated or applied, either alone or in combination, with one or more pesticides or plant growth regulants. Pesticides used in combination may be herbicides, insecticides or other fungicides or a combination thereof. When the formula I compounds are applied in combination with another pesticide or pesticides, they may be applied simultaneously or sequentially. Among the available fungicides which may be used in combination with formula I compounds are 4,6-dinitro-o-cresol, benalaxyl, benomyl, captafol, captan, carbendazim, chlorothalonil, copper, cymoxanil, dichlofluanid, dichlone, difenoconazole, dimethomorph, diniconzole, dinocap, dithianon, fenpiclonil, fenpropimorph, hymexazol, imazalil, kresoxim-methyl, azoxystrozin, fenpropidine, tridemorph, pyrimethanil, cyprodinil, fluazinam, iprodione, isoprothiolane, kasugamycin, mancozeb, mepronil, mercuric oxide, oxadixyl, oxolinic acid, penconazole, propineb, pyrifenox, thiabendazole, thiram, tolclofos-methyl, triadimefon, triflumizole, triforine, validamycin A, vinclozolin, zineb, ziram, and the like. The fungicidal compositions of the invention may be prepared by well-established procedures, e.g. intensive mixing and/or grinding of the active ingredients with other substances, such as fillers, solvents, solid carriers, and optionally surface-active compounds (tensides). Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl 2-pyrrolidone, dimethyl sulphoxide, alkyl formamides, epoxidized vegetable oils, e.g. epoxidized coconut or soybean oil, water.

Solid carriers, which may be used for dusts or dispersible powders, may be mineral fillers, such as calcite, talc, kaolin, montmorillonite, attapulgite. The physical properties may be improved by addition of highly dispersed silica gel or highly dispersed polymers. Carriers for granulates may be porous material, e.g. pumice, broken brick, sepiolite, bentonite, non-sorptive carriers may be calcite or sand. Additionally, a multitude of pre-granulated inorganic or organic materials may be used, such as dolomite or crushed plant residues.

Suitable surface-active substances may be non-ionogenic, anionic or cationic tensides with good dispersing, emulgating and wetting properties depending on the nature of the enolether compound to be formulated. Tensides may also mean mixtures of tensides. Suitable tensides may be so-called water-soluble soaps as well as water-soluble synthetic surface-active compounds. Soaps usually are alkali, earth alkali or optionally substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyl-taurine salts of fatty acids may be used. However, so-called synthetic tensides are preferably used, especially fatty sulphonates, fatty sulphates, sulphonated benzimidazole derivatives or alkyl aryl sulphonates. The fatty sulphates or fatty sulphonates are normally used as alkali, earth alkali or optionally substituted ammonium salts and have an alkyl moiety of 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. This also includes the salts of sulphuric acid esters, sulphonic acids and adducts of fatty alcohols and ethylene oxide. The sulphonated benzimidazole derivatives preferably contain 2 sulphonic acid residues and a fatty acid residue with 8 to 22 carbon atoms. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde. Furthermore, phosphates, such as the salts of the phosphoric acid ester of a p-nonylphenol-(4–14)-ethylene oxide adduct or phospholipids, may be used. Non-ionic tensides are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols. Other suitable non-ionic tensides are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit. Examples of non-ionic tensides are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol. Furthermore, fatty acid esters of polyoxy ethylene sorbitan, such as polyoxy ethylene sorbitan trioleate may be used.

Cationic tensides preferably are quaternary ammonium salts, which have at least one alkyl residue with 8 to 22 carbon atoms and, furthermore, low, optionally-halogenated alkyl, benzyl or hydroxyalkyl residues. The salts are preferably halides, methyl sulphates or alkyl sulphates, e.g. stearyl trimethyl ammonium chloride or benzyl bis(2-chloroethyl) ethyl ammonium bromide.

The tensides generally used for compositions of the invention are disclosed in publications such as:

"McCutheon's Detergents and Emulsifiers Annual", MC Publishing Corp., Ridgewood, N.J., U.S.A. 1981;

H. Stache, "Tensid-Taschenbuch", 2nd ed., C. Hanser, Munich, Vienna, 1981;

M. and J. Ash, "Encyclopedia of Surfactants", vol. I–III, Chemical Publishing Co., New York, N.Y., U.S.A. 1980–1981.

The pesticidal compositions of the invention may comprise 0.1% to 95%, preferably 0.1% to 80% of at least one compound of formula I or Ia, 1% to 99.9% of a solid or liquid adjuvant and 0% to 25%, preferably 0.1% to 25%, of a tenside.

Examples of compositions according to the invention are:

Emulsion Concentrates

Active ingredient: 1% to 20%, preferably 5% to 10%

Surface-active substance: 5% to 30%, preferably 10% to 20%

Liquid carrier: 50% to 94%, preferably 70% to 85%

Suspension-Concentrates

Active ingredient: 5% to 75%, preferably 10% to 50%

Water: 94% to 24%, preferably 88% to 30%

Surface-active substance: 1% to 40%, preferably 2% to 30%

Wettable Powder

Active ingredient: 0.5% to 90%, preferably 1% to 80%

Surface-active substance: 0.5% to 20%, preferably 1% to 15%

Solid carrier: 5% to 95%, preferably 15% to 90%

Dusts

Active ingredient: 0.1% to 10%, preferably 0.1% to 1%

Solid carrier: 99.9% to 90%, preferably 99.9% to 99%

Granulates

Active ingredient: 0.5% to 30%, preferably 3% to 15%

Solid carrier: 99.5% to 70%, preferably 97% to 85%

The fungicidal compositions can be manufactured and marketed in a concentrated form although the end-user generally employs a diluted composition. The compositions can be diluted to a concentration of 0.001% of active ingredient (a.i.). The doses usually are in the range from 0.01 to 5 kg, preferrably from 0.05 to 2 kg a.i./ha.

The compositions may also comprise other auxiliaries such as stabilizers, defoamers, viscosity controlling agents, thickeners, adhesives, fertilisers or other active ingredients to obtain special effects.

The following examples illustrate the preparation of the starting materials.

Example A 3-(3,4-Dimethoxyphenyl)acrylic acid ethyl ester 16.5 g (0.55 mol) of sodium hydride (80%) are stirred in 500 ml of tetrahydrofuran and 123.3 g (0.55 mol) of phosphonoacetic acid triethyl ester are added dropwise to give a clear solution. Then over 15 minutes a solution of 83.1 g (0.50 mol) of 3,4-dimethoxybenzaldehyde in 200 ml of tetrahydrofuran are added. The mixture is then stirred under reflux for 30 minutes. After cooling, the clear solution is separated from the insoluble material which is dissolved in 500 ml of water and extracted twice with 250 ml of toluene. The tetrahydrofuran solution is evaporated to dryness and the residue is dissolved in the toluene extract. This solution is washed three times with water, dried and the solvent evaporated.

Yield 114.6 g (97%), mp. 54° C.

Example B 2,3-Dibromo-3-(3,4-dimethoxyphenyl)propionic acid ethyl ester 59.1 g (0.25 mol) of 3-(3,4-dimethoxyphenyl)acrylic acid ethyl ester are dissolved in 125 ml of trichloromethane and cooled in an ice bath with stirring. Over 30 minutes a solution of 40.0 g (0.25 mol) of bromine in 25 ml of trichloromethane is added dropwise and stirred for a further 30 minutes at room temperature. The solvent is then evaporated at 45° C., the residue is dissolved with warming in 200 ml of cyclohexane. Upon cooling and stirring the product crystallizes. It is filtered off and washed with cyclohexane.

Yield 71.2 g (72%), mp. 106.5° C.

Example C 3-(3,4-Dimethoxyphenyl)prop-2-ynoic acid

To a solution of 52.7 g (0.80 mol) of potassium hydroxide (85%) in 300 ml of ethanol and 30 ml of water 59.4 g (0.15 mol) of 2,3-dibromo-3-(3,4-dimethoxyphenyl)propionic acid ethyl ester are added at 25° C. over 10 minutes. The mixture is stirred under reflux for 2.5 hours. The solvent is evaporated, the residue dissolved in 200 ml of water and, with cooling to 10° C., the solution acidified with 2N hydrochloric acid. The resulting crystals are filtered off, washed with water and recrystallized from methanol/water.

Yield 19.2 g (62%), mp. 155° C. (decomp.).

Example D

3-Chloro-3-(3,4-dimethoxyphenyl)-1-morpholin-4-ylprop-2-en-1-one 20.6 g (0.1 mol) of 3-(3,4-Dimethoxyphenyl)prop-2-ynoic acid and 36 ml (0.5 mol) of thionylchloride are stirred at room temperature for 2 hours. The excess thionylchloride is evaporated and the residue dissolved in 50 ml of toluene. This solution is added under ice cooling and stirring to a solution of 50 ml of pyridine and 10.9 g (0.125 mol) of morpholine in 100 ml of toluene. After 10 minutes of further stirring at room temperature the mixture is heated to 90° C. for 10 minutes. The mixture is cooled and then extracted twice with 250 ml of 2N hydrochloric acid and once with water, dried and evaporated. The resulting compound is purified by flash column chromatography using as eluant 1000 ml of toluene/acetone (10 and 20% of acetone). The fractions with Rf-value 0.52 and 0.43 in TLC (toluene/acetone 7:3) are gathered and the solvent is evaporated.

Yield 12.4 g (40%), of a yellow oil (mixture of both isomers).

The invention is described in the following examples:

Example 1

3-(4-Chlorobenzyloxy)-3-(3,4-dimethoxyphenyl)-1-morpholin-4-ylprop-2-en-1-one 0.3 g (10 mmol) of sodium hydride (80%) are stirred in 15 ml of tetrahydrofuran and 1.42 g (10 mmol) of 4-chlorobenzyl alcohol in 10 ml of tetrahydrofuran are added dropwise. The resulting clear solution is evaporated to dryness and a solution of 2.02 g (6.5 mmol) of 3-chloro-3-(3,4-dimethoxyphenyl)-1-morpholin-4-ylprop-2-en-1-one in 25 ml of dimethylformamide is added. The mixture is stirred at 90° C. for 20 hours. The solvent is then evaporated and the residue shaken with toluene/water. The organic phase is separated, washed with water, dried and purified over a flash column with 40 g of silicagel. Elution is carried out with toluene containing 10, 20 and 30% of acetone. The fractions with the TLC Rf-values 0.45 and 0.31 (toluene/acetone 7:3) are collected and evaporated.

Yield 2.45 g (90%) of an oil, which slowly crystallizes. Mp. 92°–105° C. (isomer-ratio 64/36); mp. 123° C. (E-isomer).

Example 2

3-(4-Chlorobenzylsulfanyl)-3-(3,4-dimethoxyphenyl)-1-morpholin-4-ylprop-2-en-1-one 3.17 g (20 mmol) of 4-chlorobenzylmercaptan are dissolved in 20 ml of methanol containing 3.60 g (20 mmol) of sodium methylate (30%), warmed to 50° C. and then evaporated. A solution of 4.68 g (15 mmol) of 3-chloro-3-(3,4-dimethoxyphenyl)-1-morpholin-4-ylprop-2-en-1-one in 20 ml of dimethylformamide is added. At the end of the exothermic reaction the solution is stirred at 100° C. for 1 hour and the solvent is evaporated. The residue is shaken with toluene/water, the organic phase is washed with water, dried and the reaction product is purified by flash column (150 g of silicagel) chromatography; elution with 1000 ml of toluene containing 10 and 20% of acetone. The fractions with TLC Rf-values 0.45 and 0.38 (toluene/acetone 7:3) are collected and evaporated.

Yield 4.1 g (63%) of a colourless oil (isomer-ratio 45/55).

The compounds listed in TABLES 1 to 3 below, can be prepared analogously to the above examples.

TABLE 1

Compounds of formula I, wherein $R_2$ and $R_3$ are hydrogen, and Q' is morpholin-4-yl:

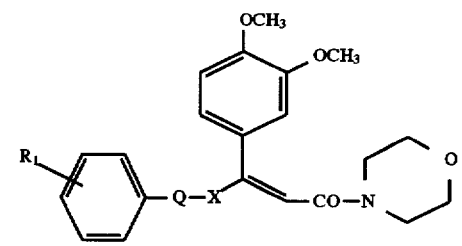

| No. | Q—X | $R_1$ | E/Z ratio or Z/E-ratio | mp (°C.) |
|---|---|---|---|---|
| 1 | $CH_2$—S | H | 30/70 | bright yellow oil |
| 2 | $CH_2$—O | 4-$C_6H_5$ | | oil |
| 3 | $CH_2$—O | 4-i-$C_3H_7$ | | oil |
| 4 | $CH(C_6H_5)$—O | H | | 104–10 |
| 5 | $CH_2$—$CH_2$—O | H | 30/70 | bright yellow oil |
| 6 | $CH_2$—$CH_2$—S | H | 45/55 | bright yellow oil |
| 7 | $CH(CH_3)$-O | H | | oil |
| 8 | $CH_2$—$CH_2$—$CH_2$—O | H | 33/67 | bright yellow oil |

TABLE 1-continued

Compounds of formula I, wherein $R_2$ and $R_3$ are hydrogen, and Q' is morpholin-4-yl:

| No. | Q—X | $R_1$ | E/Z ratio or Z/E-ratio | mp (°C.) |
|---|---|---|---|---|
| 9 | $CH_2$—O | H | | |
| 10 | $CH_2$—O | 2-Cl | | |
| 11 | $CH_2$—O | 3-Cl | | |
| 12 | $CH(CH_3)$—O | 4-Cl | | |
| 13 | $CH_2$—O | 4-F | | |
| 14 | $CH_2$—O | 4-Br | | |
| 15 | $CH_2$—O | 4-I | | |
| 16 | $CH_2$—O | 3-$OCH_3$ | | |
| 17 | $CH_2$—O | 4-$OCH_3$ | | |
| 18 | $CH_2$—O | 4-$OC_2H_5$ | | |
| 19 | $CH_2$—O | 4-O-n-$C_3H_7$ | | |
| 20 | $CH_2$—O | 4-O-n-$C_4H_9$ | | |
| 21 | $CH_2$—O | 4-$OCF_3$ | | |
| 22 | $CH_2$—O | 4-$CF_3$ | | |
| 23 | $CH_2$—O | 4-$CH_3$ | | |
| 24 | $CH_2$—O | 4-$C_2H_5$ | | |
| 25 | $CH_2$—O | 4-n-$C_3H_7$ | | |
| 26 | $CH_2$—O | 4-n-$C_4H_9$ | | |
| 27 | $CH_2$—O | 2-$CH_3$ | | |
| 28 | $CH_2$—O | 4-i-$C_4H_9$ | | |
| 29 | $CH_2$—O | 4-t-$C_4H_9$ | | |
| 30 | $CH_2$—O | 4-O-i-$C_3H_7$ | | |
| 31 | $CH_2$—S | 4-O-$C_2H_5$ | | |
| 32 | $CH_2$—O | 4-O-i-$C_4H_9$ | | |
| 33 | $CH_2$—O | 4-O-t-$C_4H_9$ | | |
| 34 | $CH_2$—S | 4-O-n-$C_3H_7$ | | |
| 35 | $CH_2$—S | 4-O-i-$C_3H_7$ | | |
| 36 | $CH_2$—S | 4-n-$C_4H_9$ | | |
| 37 | $CH_2$—S | 4-i-$C_4H_9$ | | |
| 38 | $CH_2$—S | 4-t-$C_4H_9$ | | |
| 39 | $CH_2$—S | 4-$OCH_3$ | | |
| 40 | $CH_2$—S | 4-F | | |
| 41 | $CH_2$—S | 4-Br | | |
| 42 | $CH_2$—S | 4-$C_6H_5$ | | |
| 43 | $CH_2$—S | 4-$CH_3$ | | |
| 44 | $CH_2$—S | 4-$C_2H_5$ | | |
| 45 | $CH_2$—S | 2-Cl | | |
| 46 | $CH_2$—S | 3-Cl | | |
| 47 | $CH_2$—S | 2-$OCH_3$ | | |
| 48 | $CH_2$—S | 4-n-$C_3H_7$ | | |
| 49 | $CH_2$—S | 4-i-$C_3H_7$ | | |
| 50 | $CH_2$—S | 4-$CF_3$ | | |
| 51 | $CH_2$—S | 4-$OCF_3$ | | |
| 52 | $CH_2$—S | 4-O-n-$C_4H_9$ | | |
| 53 | $CH_2$—S | 4-O-i-$C_4H_9$ | | |
| 54 | $CH_2$—S | 4-O-t-$C_4H_9$ | | |
| 55 | $CH_2$—S | 4-I | | |
| 56 | $CH_2$—O | 4-$CH(CH_3)$—$C_2H_5$ | | |
| 57 | $CH_2$—S | 4-$CH(CH_3)$—$C_2H_5$ | | |

TABLE 2

Compounds of formula I, wherein $R_3$ is hydrogen and Q' is morpholin-4-yl:

| No. | Q—X | $R_1$ | $R_2$ |
|---|---|---|---|
| 1 | $CH_2$—O | 2-Cl | 3-Cl |
| 2 | $CH_2$—O | 2-Cl | 4-Cl |
| 3 | $CH_2$—O | 2-Cl | 5-Cl |
| 4 | $CH_2$—O | 2-Cl | 6-Cl |
| 5 | $CH_2$—O | 3-Cl | 4-Cl |
| 6 | $CH_2$—O | 3-Cl | 5-Cl |
| 7 | $CH_2$—O | 2-$CH_3$ | 3-$CH_3$ |
| 8 | $CH_2$—O | 2-$CH_3$ | 4-$CH_3$ |
| 9 | $CH_2$—O | 2-$CH_3$ | 5-$CH_3$ |
| 10 | $CH_2$—O | 2-$CH_3$ | 4-Cl |
| 11 | $CH_2$—S | 2-Cl | 4-Cl |

TABLE 3

Compounds of formula I, wherein $R_2$ and $R_3$ are hydrogen and Q' is NR'R":

| No. | Q—X | $R_1$ | R' | R" |
|---|---|---|---|---|
| 1 | $CH_2$—O | H | $CH_3$ | $CH_3$ |
| 2 | $CH_2$—O | 4-Cl | $CH_3$ | $CH_3$ |
| 3 | $CH_2$—O | 4-$C_6H_5$ | $CH_3$ | $C_2H_5$ |
| 4 | $CH_2$—O | 4-$CF_3$ | $CH_3$ | $CH_3$ |
| 5 | $CH_2$—O | 4-$OCF_3$ | $CH_3$ | $C_2H_5$ |
| 6 | $CH_2$—O | H | $CH_3$ | $C_2H_5$ |
| 7 | $CH_2$—O | 4-Cl | $C_2H_5$ | $C_2H_5$ |
| 8 | $CH_2$—O | 4-$C_6H_5$ | $C_2H_5$ | $C_2H_5$ |
| 9 | $CH_2$—O | 4-i-$C_3H_7$ | $C_2H_5$ | $C_2H_5$ |
| 10 | $CH_2$—S | 4-Cl | $CH_3$ | $C_2H_5$ |
| 11 | $CH_2$—O | 4-Cl | $CH_3$ | $C_2H_5$ |

Biological Testing

A. Determination of minimal inhibition concentration (MIC value)

Ten test tubes (16×60 mm, with aluminum cap, Schott, Mainz, FRG) per compound were filled with nutrient solution (V8-juice, 3 ml) and autoclaved. After cooling down, sterile nutrient solution (3 ml) containing the active compound (200 µg/ml) was pipetted into the first tube and mixed. Then, half the content of the first tube (3 ml) was transferred to the second tube, mixed and, again, half the content of this tube transferred to the third and so on. By this means, the following series of test solutions was prepared, as shown in Table 4.

TABLE 4

| Tube No. | Concentration (a.i. μg/ml) |
|---|---|
| 1 | 100 |
| 2 | 50 |
| 3 | 25 |
| 4 | 12.5 |
| 5 | 6.25 |
| 6 | 3.13 |
| 7 | 1.56 |
| 8 | 0.78 |
| 9 | 0.39 |
| 10 | 0.2 |

The tubes were inoculated by transferring nutrient agar slices (5 mm diam.) from a *Phytophthora infestans* agar culture into the tubes. After an incubation time of 7 days at 18° C., the assessment was carried out by visual inspection of the test tubes. The lowest concentration in the test tubes without mycelium growth was recorded as minimal inhibition concentration. The results are shown in Table 5, below.

TABLE 5

| Test compound (Example or TABLE/No.) | MIC [ppm] |
|---|---|
| Example 1 (isomer ratio 64/36) | 1.56 |
| Example 1 (E-isomer) | 0.78 |
| T1/2 | 0.39 |
| T1/3 | 0.39 |
| T1/4 | >100 |
| T1/5 | 12.5 |
| T1/6 | 0.39 |
| T1/7 | >100 |
| T1/8 | 12.5 |

B. Evaluation of the protective activity of fungicides for the control of grape downy mildew Grape seedlings (*Vitis vinifera*) with 2–3 mature leaves were used for the test. All technical grade compounds were formulated in a solvent surfactant system containing 5% acetone, 0.05% Tween 20 and deionized water. Formulated test compounds were applied to all foliar surfaces to the point of run-off. For the Primary (initial) screens 200 ppm a.i. solution was used. For the Secondary screens, concentrations of 200, 50 and 12.5 ppm a.i. were applied. The plants were allowed to dry 2–5 hours prior to inoculation.

A hand-held De Vilbiss atomizer was used to inoculate the foliage with a sporangial suspension of the grape downy mildew fungus, targeting the undersites of the leaves. 1.5 ml suspension was required per plant. <Inoculated plants were placed into a moisture chamber (22° C.; 100% rel. humidity) for 24 hours. The plants were then moved to the greenhouse. 7–10 days after inoculation a 24 hours incubation period in a moisture chamber induced sporulation.

Evaluation was made using the following Rating system:

| Disease Control | |
|---|---|
| Rating | % Control |
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |
| | Rating not possible |

The evaluation results are shown in Table 6.

TABLE 6

| Test compound (Example or Table/No.) | Disease Control Rating | | |
|---|---|---|---|
| | 200 ppm | 50 ppm | 12.5 ppm |
| Example 1 (isomer ratio 64/36) | 8 | 7 | 6 |
| Example 1 (E-isomer) | 9 | 9 | 5 |
| Example 2 | 5 | | |
| T1/2 | 5 | | |
| T1/3 | 6 | | |
| T1/4 | 6 | | |
| T1/6 | 4 | | |

We claim:

1. A compound of the formula

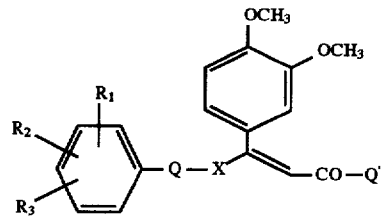

wherein Q represents a group of formula $(CH_2)_m$ (wherein m is 2 or 3) or CH—R (wherein R represents a hydrogen atom, a phenyl or a straight or branched $C_1$–$C_4$ alkyl group); Q' represents a morpholin-4-yl, a dimethylamino, methylethylamino or diethylamino group; $R_1$ represents a hydrogen or halogen atom, a phenyl or a straight or branched $C_1$–$C_6$ alkyl or alkoxy group optionally substituted by one or more halogen atoms; $R_2$ and $R_3$ independently represent a hydrogen or halogen atom, a straight or branched $C_1$–$C_6$ alkyl or alkoxy group optionally substituted by one or more halogen atoms; and X represents an oxygen or sulphur atom.

2. A compound according to claim 1, wherein Q' represents morpholin-4-yl.

3. A compound according to claim 1, wherein Q represents CH—R and R is a hydrogen atom.

4. A compound according to claim 1, wherein X represents an oxygen atom.

5. A compound according to claim 1, wherein $R_3$ is a hydrogen atom.

6. A compound according to claim 1, wherein $R_2$ and $R_3$ both are hydrogen atoms.

7. A compound according to claim 1, wherein $R_1$ represents a hydrogen, fluorine, chlorine or bromine atom, a $C_1$–$C_4$ alkyl or alkoxy group, a phenyl group, or a trifluoromethyl or trifluoromethoxy group.

8. A compound according to claim 1, wherein $R_2$ and $R_3$ are hydrogen atoms and $R_1$ represents a hydrogen or fluorine, chlorine or bromine atom, a $C_1$–$C_4$ alkyl or alkoxy group, a trifluoromethyl or trifluoromethoxy group.

9. 3-(4-Chlorobenzyloxy)-3-(3,4-dimethoxyphenyl)-1-morpholin-4-ylprop-2-en-1-one, as either an E or Z isomer, or as a mixture comprising the E and Z isomer.

10. 3-(4-i-Propylbenzyloxy)-3-(3,4-dimethoxyphenyl)-1-morpholin-4-ylprop-2-en-1-one, as either an E or Z isomer, or as a mixture comprising the E and Z isomer.

11. A process for preparing the compound according to claim 1 which comprises reacting a compound of formula

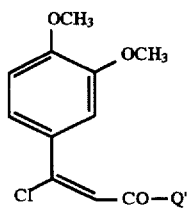

(II)

with an alcohol or thiol of formula

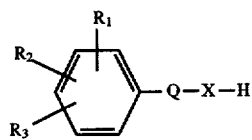

(III)

in the form of an alkali metal salt, to form either an E or Z isomer, or a mixture comprising the E or Z isomer; and isolating the E or Z isomer, or mixture by crystallisation or chromatography.

12. A fungicidal composition comprising a compound of claim 1, and either or both a carrier and additive.

13. A method of combating fungi at a locus which comprises treating the locus with an effective amount of the compound of claim 1.

14. A method of combating fungi comprising applying a composition having an effective amount of the compound of claim 1 to phytopathogenic fungi in agriculture.

15. The method of claim 14 wherein the phytopathogenic fungi is *Phytophthora infestans* or *Plasmopara viticola*.

* * * * *